United States Patent
Hong

(10) Patent No.: US 10,463,703 B2
(45) Date of Patent: Nov. 5, 2019

(54) FERMENTED COMPOSITION FOR RELIEVING ATOPIC DERMATITIS CONTAINING NATURAL EXTRACTS

(71) Applicant: Truezyme Co., Ltd., Ulsan (KR)

(72) Inventor: Kyu Ree Hong, Ulsan (KR)

(73) Assignee: TRUEZYME CO., LTD., Ulsan (KR)

( * ) Notice: Subject to any disclaimer, the term of this patent is extended or adjusted under 35 U.S.C. 154(b) by 165 days.

(21) Appl. No.: 15/820,323

(22) Filed: Nov. 21, 2017

(65) Prior Publication Data

US 2018/0140646 A1     May 24, 2018

(30) Foreign Application Priority Data

Nov. 22, 2016    (KR) .................... 10-2016-0155831

(51) Int. Cl.
| | | |
|---|---|---|
| *A61K 36/00* | (2006.01) |
| *A61K 35/745* | (2015.01) |
| *A61K 9/00* | (2006.01) |
| *A61K 36/03* | (2006.01) |
| *A61K 36/282* | (2006.01) |
| *A61K 36/752* | (2006.01) |
| *A61K 36/82* | (2006.01) |
| *A61K 9/06* | (2006.01) |

(52) U.S. Cl.
CPC .......... *A61K 35/745* (2013.01); *A61K 9/0014* (2013.01); *A61K 9/06* (2013.01); *A61K 36/03* (2013.01); *A61K 36/282* (2013.01); *A61K 36/752* (2013.01); *A61K 36/82* (2013.01); *A61K 2236/19* (2013.01); *A61K 2236/333* (2013.01)

(58) Field of Classification Search
None
See application file for complete search history.

(56) References Cited

FOREIGN PATENT DOCUMENTS

KR     2011016611 A   *   2/2011

* cited by examiner

*Primary Examiner* — Qiuwen Mi
(74) *Attorney, Agent, or Firm* — Novick, Kim & Lee, PLLC; Jae Youn Kim

(57) ABSTRACT

Provided is a composition for external skin application, the composition configured for relieving atopic dermatitis, including a mixed extract consisting of a *Bifidobacterium*-fermented extract, a citrus (*Citrus unshiu Marcov.*) peel extract, a *Laminaria japonica* extract, a *Camellia Japonica L.* extract, and an *Artemisia argyi* extract as an active ingredient.

15 Claims, No Drawings

FERMENTED COMPOSITION FOR RELIEVING ATOPIC DERMATITIS CONTAINING NATURAL EXTRACTS

CROSS-REFERENCE TO RELATED APPLICATION

This application claims priority to and the benefit of Korean Patent Application No. 2016-0155831, filed on Nov. 22, 2016, the disclosure of which is incorporated herein by reference in its entirety.

BACKGROUND

1. Field of the Invention

The present invention relates to a composition for relieving atopic dermatitis containing natural extracts.

2. Discussion of Related Art

The epidermis, which is the outer layer of the two main layers that make up the skin, protects the human body from the outside. The stratum corneum, which is the outermost layer of the epidermis, acts as a barrier, inhibiting moisture evaporation or loss from the epidermis (preventing drying), and also preventing bacteria, fungi, viruses, and the like from penetrating the skin. The stratum corneum is composed of two components, corneocytes (terminally differentiated keratinocytes) and lipid-enriched lamellar membrane structures. The architecture of the stratum corneum is referred to as "bricks (corneocytes) and mortar (lamellar membranes)". Several layers of corneocytes are present in the stratum corneum.

Atopic dermatitis is a skin disorder with symptoms such as strong pruritus with unclear causes, dryness, severe keratinization, scalp squama (dandruff), erythema and turgidity, skin crack, severe oozing and eczema, lichenification, and the like. Atopic dermatitis is generally considered to be a chronic disease, lasting more than 10 years and causing great discomfort. Previously, in most cases, after atopic dermatitis occurred in infancy or early childhood, the symptoms gradually disappeared before the age of 7 to 8 years. However, since the 1970s, the incidence of atopic dermatitis has increased year by year due to pollution caused by rapid industrialization, environmental pollution, and the like. Symptoms of atopic dermatitis that emerges during childhood tend to persist until adolescence and adulthood and gradually worsen. In addition, the incidence of atopic dermatitis after adolescence has also increased remarkably. The main symptom of atopic dermatitis is skin inflammation with strong pruritus, and the main cause of pruritus is histamine hypersecretion. Scratching the skin due to pruritus may lead to erythema or eczema lesions, and in severe cases, the skin may peel off or lichenification (thickening of the skin) may occur.

Until recently, research results and information about the causes of atopic dermatitis have been reported. However, the reported research data are contradictory, which may be due to the complexity of atopic dermatitis itself. Therefore, clear causes and effective treatment methods for atopic dermatitis have not yet been clearly established.

Due to these problems, therapeutic agents that alleviate symptoms to some extent, rather than fundamental treatment, have been used to treat atopic dermatitis. Examples of the therapeutic agents include steroid preparations, oral antihistamines, hydroxyquinoline, tar preparations, and hypoallergenic moisturizers. However, none of the medicines developed so far can completely treat patients with atopic dermatitis.

Meanwhile, cosmetics for relieving atopic dermatitis should basically not cause pruritus and skin irritation, and should have functions such as a skin soothing effect, inflammation inhibition, bacterial growth suppression, moisturization, and skin barrier maintenance.

However, research has shown that chemical preservatives (e.g., parabens, phenoxyethanol, and diazolidinyl urea) used in cosmetics for relieving atopic dermatitis developed so far cause DNA damage. In addition, these preservatives have been reported to exacerbate the symptoms of atopic dermatitis.

Thus, to reduce side effects such as skin irritation, there is increasing demand for cosmetics containing natural ingredients, with a minimal amount of chemical ingredients. Accordingly, research is actively being carried out to develop cosmetics for relieving atopic dermatitis having excellent in vivo biostability and an excellent skin soothing effect.

SUMMARY OF THE INVENTION

Therefore, the present invention has been made in view of the above problems, and it is an objective of the present invention to provide a composition for external skin application, which includes natural raw materials as active ingredients and has anti-inflammatory activity. According to the present invention, the composition may be beneficial to skin health and may exert an excellent skin soothing effect.

In accordance with the present invention, the above and other objectives can be accomplished by the provision of a composition for external skin application for relieving atopic dermatitis, including a mixed extract consisting of a *Bifidobacterium*-fermented extract, a citrus (*Citrus unshiu Marcov.*) peel extract, a *Laminaria japonica* extract, a *Camellia Japonica L.* extract, and an *Artemisia argyi* extract as an active ingredient.

In one embodiment, the mixed extract may contain 10 to 20 parts by weight of the *Bifidobacterium*-fermented extract, 10 to 20 parts by weight of the citrus (*Citrus unshiu Marcov.*) peel extract, 10 to 20 parts by weight of the *Laminaria japonica* extract, 10 to 20 parts by weight of the *Camellia Japonica L.* extract, and 10 to 20 parts by weight of the *Artemisia argyi* extract.

In one embodiment, the composition may contain 0.5 to 10.0% by weight of the mixed extract.

In one embodiment, the mixed extract may be extracted using one or more solvents selected from the group consisting of purified water, a lower alcohol having 1 to 4 carbon atoms, acetone, ethyl acetate, butyl acetate, and 1,3-butylene glycol.

In one embodiment, the alcohol may be 60 to 90% (v/v) ethanol.

In one embodiment, the composition may have antioxidant, anti-inflammatory, and antimicrobial activities.

In one embodiment, the composition may be formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

DETAILED DESCRIPTION OF EXEMPLARY EMBODIMENTS

Although the terms used in the present invention are selected from generally known and used terms, terms used herein may be variable depending on operator's intention or customs in the art, appearance of a new technology, or the like. In addition, some of the terms mentioned in the description of the present invention have been selected by the applicant at his or her discretion, the detailed meanings of which are described in relevant parts of the description herein. Furthermore, it is required that the present invention is understood, not simply by the actual terms used but by the meanings of each term lying within.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The numerical range includes numerical values defined in the above range. All maximum numerical limitations given throughout this specification include all lower numerical limitations, as lower numerical limitations are explicitly stated. All minimum numerical limitations given throughout this specification include all higher numerical limitations as higher numerical limitations are explicitly stated. All numerical limitations given throughout this specification will include any better numerical range within broader numerical range, as narrower numerical limitations are explicitly stated.

Hereinafter, embodiments of the present invention will be described in detail, but it should be apparent that the present invention is not limited by the following embodiments.

According to an aspect of the present invention, provided is a composition for external skin application for relieving atopic dermatitis including a mixed extract consisting of a *Bifidobacterium*-fermented extract, a citrus (*Citrus unshiu Marcov.*) peel extract, a *Laminaria japonica* extract, a *Camellia Japonica L.* extract, and an *Artemisia argyi* extract, as an active ingredient.

The composition for external skin application contains a mixed extract derived from natural raw materials as an active ingredient and has excellent antioxidant, anti-inflammatory, and antimicrobial activities. Thus, the composition may effectively alleviate atopic dermatitis while minimizing skin irritation. In particular, since the components of the mixed extract act on the skin simultaneously, effects such as soothing of the skin and relieving of atopic dermatitis may be remarkably increased.

The *Bifidobacterium*-fermented extract refers to a mixture of fermented products obtained by fermenting a medium containing an energy source such as skim milk powder using a *Bifidobacterium* strain. The fermented products may be prepared by a conventional fermentation method using lactic acid bacteria. The fermentation method using lactic acid bacteria is well known to those skilled in the art.

The energy source may be cow milk, goat milk or horse milk, and these milks may be used in the form of whole milk, skim milk or powdered milk.

The *Bifidobacterium* strain may be Bifidobacterium breve, *Bifidobacterium bifidum*, *Bifidobacterium longum* or *Bifidobacterium infantis*, without being limited thereto.

The *Bifidobacterium* strain mainly uses oligosaccharides containing amino sugars, inhibits the growth of harmful bacteria in the intestines, promotes digestion and absorption of proteins, and provides vitamins to the body. The *Bifidobacterium*-fermented extract promotes conversion of profilaggrin, the precursor of a natural moisturizing factor (NMF), into NMF, thereby improving skin moisturizing and imparting moisture and shine to the skin. In addition, rich polysaccharide components contained in the fermented extract may inhibit water evaporation at the skin surface.

The *Bifidobacterium*-fermented extract may contain the fermented product of green tea leaves.

Green tea leaves contain a large amount of catechin and have excellent antimicrobial and anti-cancer effects, and contains vitamin C, vitamin E, beta-carotene, plant fiber, minerals, and chlorophyll. Green tea leaves have various effects such as an antioxidant effect, a skin elasticity improvement effect, an anti-aging effect, a heavy metal removal effect, an anti-allergic effect, an anti-inflammatory effect, and an immunity strengthening effect. In particular, by fermenting green tea leaves using the Bifidobacterium strain, the antioxidant effect and the skin elasticity improvement effect of green tea leaves may be further increased.

The term "*Citrus unshiu Marcov.*" is rich in vitamin C and citric acid, and contains vitamin P, phosphorus, and hesperidin, which are excellent in strengthening capillary blood vessels. The active ingredients are more abundant in the peel than in the flesh, and for example, vitamin C is about four times more abundant in the peel than in the flesh. The citrus (*Citrus unshiu Marcov.*) peel extract has an excellent effect of neutralizing IL-8, an inflammatory cytokine, and neutralizes melanocyte- stimulating substances, thereby inhibiting melanin production. Thus, the citrus (*Citrus unshiu Marcov.*) peel extract may help to make the skin healthy and clean.

The term "*Laminaria japonica*" is perennial large brown algae belonging to a division of Phaeophyta, a class of Phaeophyceae, an order of Laminariales, and a family of Laminariaceae, and is also called true sea tangle, "HAEDAE" or "HAEGONPO". *Laminaria japonica* is a type of marine algae distributed in the coasts of polar zones and subpolar zones and inhabits cold seas, and since ancient times, *Laminaria japonica* has been used for edible or medicinal purposes in Korea, Japan, and China. The *Laminaria japonica* extract may provide vitality to the damaged skin and alleviate skin irritation. In addition, the extract may inhibit excessive secretion of sebum, giving the skin a refreshing feeling and improving skin health.

The term "*Camellia Japonica L.*" is the flower of an evergreen arborescent camellia belonging to Theaceae, and is also called "SANDAWA". *Camellia Japonica L.* is the flower of an evergreen arborescent camellia that lives in the mountains and villages near the coasts of the southern part of the Republic of Korea, Ulleungdo and Daecheongdo, and contains large amounts of leucoanthocyanin and anthocyanin. In addition, *Camellia Japonica L.* contains camellin B, quercetin, campherol, sexangularetin, phenol compounds such as ρ-hydroxybenzoic acid, protocatechuic acid, and gallic acid, and the like. Thus, *Camellia Japonica L.* may increase collagen synthesis efficiency in fibroblasts and improve skin elasticity.

The term "*Artemisia argyi*" refers to medicinal substances obtained by drying the leaves and young stems of *Artemisia argyi*, *A. princeps* var. *orientalis* or *A. montana*, which belongs to Asteraceae, and is also called "AEGUCHO", "GUCHO", "CHEOMAE", "AE", "BINGDAE", "UICHO", "HWANGCHO", "AEHO", and the like. Since Artemisia argyi acts to warm aeremia and jingmai, in oriental medicine, *Artemisia argyi* is widely used to treat symptoms associated with bleeding such as uterine bleeding caused by weak and cold of the uterus and lower abdomen, bleeding during pregnancy, hematemesis, nosebleed, and hemoptysis. *Artemisia argyi* is reported to have pharmacological effects on hemostatic action, bacteriostatic action, bronchial smooth muscle relaxation, antitussive and apophlegmatic action, sleep-promoting action, uterine stimulation induction, and anaphylactic shock protection.

Through interaction of active ingredients derived from each raw material contained in the mixed extract, the mixed extract may exert a skin soothing effect and the effect of relieving atopic dermatitis. When the mixed extract is used, various components contained in each extract are applied to the skin at the same time, so that absorption of the extract is improved, and a skin soothing effect and the effect of relieving atopic dermatitis may be maximized.

The term "extract" refers to a solvent containing the active ingredients of a raw material, and may be obtained by mixing a solvent and the raw material under specific conditions. Any substance extracted from a natural raw material may be an extract regardless of extraction methods or the kind of ingredients of the natural raw material. Examples of the extract may include components (specifically, specific components such as oil) extracted by dissolving natural products in water or an organic solvent.

The mixed extract may be extracted using one or more solvents selected from the group consisting of purified water, a lower alcohol having 1 to 4 carbon atoms, acetone, ethyl acetate, butyl acetate, and 1,3-butylene glycol, and the alcohol may be 60 to 90% (v/v) ethanol.

The extraction proportion of active ingredients contained in the raw material may be varied depending on the polarity of a solvent. Since ethanol may selectively extract physiologically active substances from a natural raw material, a skin improvement effect may be realized when an extract obtained by ethanol extraction is used.

Particularly, water and ethanol have different polarities, and thus active ingredients to be extracted may be varied depending on the net polarity of the mixture of water and ethanol. Therefore, the concentration of ethanol may be appropriately controlled to enhance a skin improvement effect. At this time, when the concentration of ethanol exceeds 90%, the yield of an extract may be low. When the concentration of ethanol is less than 60%, active ingredients showing a skin improvement effect may not be extracted sufficiently.

The method of preparing the mixed extract is as follows. First, each raw material is washed with water, dried, and then pulverized. After adding a solvent having a volume corresponding to 8 to 12 times the weight of the pulverized product to the pulverized product, an extraction process is performed for about 1 to 24 hours according to a conventional extraction method. At this time, examples of the extraction method include reflux circulation extraction, pressure extraction, ultrasonic extraction, and the like. Finally, a filtration process is performed. In addition, the extract may be obtained in a powder form by an additional process such as vacuum distillation or lyophilization.

Examples of the extract may include extracts that have been subjected to a conventional purification process. Specific examples of the extract may include extracts obtained by additionally performing various purification processes such as separation using an ultrafiltration membrane having a constant molecular weight cut-off value and separation using chromatography (separation by size, charge, hydrophobicity or affinity).

The composition may contain 0.5 to 10.0% by weight of the mixed extract. When the mixed extract is contained in an amount less than 0.5% by weight, the effect of relieving atopic dermatitis by the mixed extract may not be properly realized. When the mixed extract is contained in an amount exceeding 10.0% by weight, the amounts of other additives to be contained in a product are reduced, and thus the quality of the product may deteriorate.

The mixed extract may contain 10 to 20 parts by weight of the *Bifidobacterium*-fermented extract, 10 to 20 parts by weight of the citrus (*Citrus unshiu Marcov.*) peel extract, 10 to 20 parts by weight of the *Laminaria japonica* extract, 10 to 20 parts by weight of the Camellia *Japonica L.* extract, and 10 to 20 parts by weight of the *Artemisia argyi* extract.

When the content of each active ingredient contained in the mixed extract is outside of the above range, a synergistic effect depending on interaction among the active ingredients may not be properly implemented Therefore, the mixing ratio may be appropriately controlled in consideration of the working environment and the quality of a final product.

The mixed extract may be extracted using one solvent selected from the group consisting of purified water, a lower alcohol having 1 to 4 carbon atoms, acetone, ethyl acetate, butyl acetate, and 1,3-butylene glycol, without being limited thereto.

The extraction proportion of active ingredients contained in the raw materials may be varied depending on the polarity of a solvent. Particularly, the solvent may be an alcohol having excellent selectivity in extracting physiologically active substances present in the raw material. Specifically, to achieve an optimal skin moisturizing effect, the alcohol may be 60 to 90% ethanol, without being limited thereto.

Particularly, water and ethanol have different polarities, and thus active ingredients to be extracted may be varied depending on the net polarity of the mixture of water and ethanol. Therefore, the concentration of ethanol may be appropriately controlled to enhance a skin improvement effect. At this time, when the concentration of ethanol is less than 60%, active ingredients showing a skin improvement effect may not be extracted sufficiently. When the concentration of ethanol exceeds 90%, the yield of an extract may be low. Thus, the concentration of ethanol may be appropriately adjusted within the above range.

The composition for external skin application may be used for soothing the skin or relieving atopic dermatitis, and may be formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

When the composition for external skin application is formulated into each formulation, components other than the active ingredients may be appropriately compounded within a range not impairing the object of the present invention, according to the type of the formulation, the purpose of use or the like.

Depending on the quality or function of the final product, the composition for external skin application may further include adjuvants commonly used in cosmetics or dermatology. Examples of the adjuvants may include fatty substances, organic solvents, solubilizing agents, thickening agents, gelling agents, softening agents, antioxidants, suspending agents, stabilizers, foaming agents, fragrances, surfactants, water, ionic or non-ionic emulsifiers, fillers, sequestrants, chelating agents, preservatives, blockers, wetting agents, essential oils, dyes, pigments, and hydrophilic or lipophilic activators.

However, it is preferable that the kind of the adjuvant and the mixing ratio of the adjuvant are selected within a range that does not affect the properties of the cosmetic composition according to the present invention.

Hereinafter, preferred embodiments of the present disclosure will be described in detail with reference to the following experimental results. However, the scope of the present disclosure is not limited by these embodiments.

PREPARATION EXAMPLE 1

Preparation of *Bifidobacterium* Strain-fermented Extracts

A skim milk powder medium was inoculated with a *Bifidobacterium bifidum* strain, and cultured at 37° C. for 3 days. After culture, centrifugation was performed to obtain a supernatant. The pH of the supernatant was adjusted to 6.5. The supernatant was subjected to lyophilization to obtain a fermented product. The composition of skim milk powder medium is shown in Table 1 below.

TABLE 1

| Ingredient | Concentration (g/L) |
| --- | --- |
| Skim milk powder | 100 |
| Glucose | 20 |
| Yeast extract | 3 |
| Peptone | 3 |
| Distilled water | 1 |

PREPARATION EXAMPLE 2

Preparation of *Bifidobacterium*-fermented Green Tea Leaf Extract

A fermentation medium containing glucose, sugar, starch syrup, and a yeast extract (glucose 1.5% (v/v), sugar 1.5% (v/v), starch syrup 1.5% (v/v), and yeast extract 0.3% (v/v)) was fermented using a *Bifidobacterium bifidum* strain to prepare a fermented extract.

10 mg of a *Bifidobacterium bifidum* strain (dried form) was added to the fermentation medium (10 mL), and pre-cultured. A green tea leaf extract was added to a fresh fermentation medium and fermented by inoculating the pre-culture solution.

The *Bifidobacterium bifidum* strain was cultured at 36.5° C. for 36 hours, and the contents of glucose and sugar were controlled to increase the growth rate of the strain during culture. After the fermentation was completed, centrifugation and filtering were performed to obtain a *Bifidobacterium*-fermented green tea leaf extract.

PREPARATION EXAMPLE 3

Preparation of Natural Extract (Hot Water Extraction)

Citrus (*Citrus unshiu Marcov.*) peel, *Laminaria japonica*, *Camellia Japonica L.*, mulberry root, and *Artemisia argyi* were each washed, dried at room temperature, and pulverized to obtain 100 g of a coarsely pulverized product for each component.

100 g of each of the pulverized products was immersed in purified water having a volume of 10 times the volume of the pulverized product, and reflux-extracted at 80° C. for 12 hours.

The extract was filtered through a fine filter, and the remaining raw material was extracted three times in the same manner, and then cooled at room temperature. Each of the extracts was concentrated under reduced pressure at 30° C. and lyophilized to obtain a solid matter.

PREPARATION EXAMPLE 4

Preparation of Natural Extract (Ethanol Extraction)

Each extract was obtained in the same manner as in Preparation Example 3, except that an ethanol aqueous solution (70% mass concentration) was used as an extraction solvent. Each extract was concentrated under reduced pressure and then lyophilized to obtain a solid matter.

EXAMPLE 1

Mixed Extract (Hot Water Extraction) Sample

The extracts of Preparation Examples 1 and 3 obtained by lyophilization were mixed in the same ratio. 10 g of the mixed extract was used as the sample of Example 1.

EXAMPLE 2

Mixed Extract (Ethanol Extraction) Sample

The extracts of Preparation Examples 1 and 4 obtained by lyophilization were mixed in the same ratio. 10 g of the mixed extract was used as the sample of Example 2.

EXAMPLE 3

Mixed Extract (Ethanol Extraction) Sample

The extracts of Preparation Examples 2 and 4 obtained by lyophilization were mixed in the same ratio. 10 g of the mixed extract was used as the sample of Example 3.

COMPARATIVE EXAMPLE 1

*Bifidobacterium*-fermented Extract Sample 10 g of the *Bifidobacterium*-fermented extract of Preparation Example 1 obtained by lyophilization was used as the sample of Comparative Example 1.

COMPARATIVE EXAMPLE 2

Citrus (*Citrus unshiu Marcov.*) Peel Extract (Hot Water Extraction) Sample 10 g of the citrus (*Citrus unshiu Marcov.*) peel extract of Preparation Example 1 obtained by lyophilization was used as the sample of Comparative Example 2.

COMPARATIVE EXAMPLE 3

*Laminaria japonica* Extract (Hot Water Extraction) Sample 10 g of the *Laminaria japonica* extract of Preparation Example 2 obtained by lyophilization was used as the sample of Comparative Example 3.

COMPARATIVE EXAMPLE 4

*Camellia Japonica L.* Extract (Hot Water Extraction) Sample 10 g of the *Camellia Japonica L.* extract of Preparation Example 2 obtained by lyophilization was used as the sample of Comparative Example 4.

COMPARATIVE EXAMPLE 5

*Artemisia argyi* Extract (Hot Water Extraction) Sample 10 g of the *Artemisia argyi* extract of Preparation Example 2 obtained by lyophilization was used as the sample of Comparative Example 5.

EXPERIMENTAL EXAMPLE 1

Evaluation of free radical scavenging activity

The extracts of the examples and the comparative examples were suspended in purified water (at a concentration of 10%), and the free radical scavenging activities thereof were evaluated.

DPPH assay is a method in which an inhibitor eliminates a stable radical, 2,2-diphenyl-1-picrylhydrazyl (DPPH), and the degree of discoloration is analyzed by measuring the absorbance at 540 nm.

Dibutyl hydroxy toluene (BHT) was used as a control for measurement of free radical scavenging activity. BHT is a colorless crystal or white crystalline powder, and has an excellent antioxidant effect and thus is widely used as an antioxidant for edible oil and fat, and foods containing oil or fat.

The experiment was repeated three times for accuracy, and the results are shown in Table 2 below.

TABLE 2

| Classification | DPPH radical scavenging activity (%) |
| --- | --- |
| Example 1 | 133.1 |
| Example 2 | 141.7 |
| Example 3 | 147.5 |
| Comparative Example 1 | 113.5 |
| Comparative Example 2 | 103.3 |
| Comparative Example 3 | 106.5 |
| Comparative Example 4 | 92.7 |
| Comparative Example 5 | 97.8 |
| Control Group | 155.9 |

Referring to Table 2, in the cases of Examples 1 to 3, the concentration of the extract and the free radical scavenging activity thereof were proportional, and the free radical scavenging activity was significantly superior to that of Comparative Examples 1 to 5.

High free radical scavenging activity may indicate that the antioxidant effect is excellent. In particular, the extracts of Examples 2 and 3, which were prepared using ethanol extraction, showed an excellent antioxidant effect as compared with that of Example 1.

EXPERIMENTAL EXAMPLE 2

Evaluation of Anti-inflammatory Activity

The inhibitory activity of EAME on NO production was examined in RAW 264.7 cells, a murine macrophage cell line, stimulated with lipopolysaccharide (LPS), and the anti-inflammatory activities of the extracts of the examples and the comparative examples were evaluated.

Raw 264.7 cells were obtained from the Korean Cell Line Bank. Raw 264.7 cells were cultured in a DMEM medium containing 100 units/mL penicillin-streptomycin and 10% fetal bovine serum (FBS) in a $CO_2$ incubator set to 37° C. with 5% $CO_2$, and subcultured every 2 to 3 days.

Raw 264.7 cells (at a cell density of $3 \times 10^5$ cells/mL) were pre-cultured for 18 hours, treated with the extract samples (at a concentration of 10%) of the examples and the comparative examples and LPS (1 μg/mL) at the same time, and further cultured for 24 hours. After culture, to determine the amount of produced NO, the amount of $NO_2^-$ present in the cell culture medium was measured using a Griess reagent. A negative control group was not treated with LPS, and a positive control group was treated only with LPS.

100 μL of the cell culture supernatant and 100 μL of a Griess reagent (1% (w/v) sulfanilamide and 0.1% (w/v) naphtylehtylenediamine in 2.5% (v/v) phosphoric acid) were mixed and reacted at room temperature for 10 minutes under dark conditions. After reaction, absorbance was measured at 540 nm using a ELISA reader. A standard concentration curve was obtained using serial dilution of sodium nitrite ($NaNO_2$) (10-100 μM). The results are shown in Table 3 below.

TABLE 3

| Classification | Amount of NO production (μM) |
| --- | --- |
| Example 1 | 13.47 |
| Example 2 | 11.72 |
| Example 3 | 10.37 |
| Comparative Example 1 | 22.54 |
| Comparative Example 2 | 24.94 |
| Comparative Example 3 | 23.61 |
| Comparative Example 4 | 26.53 |
| Comparative Example 5 | 25.52 |
| LPS (−) | 6.64 |
| LPS (+) | 37.21 |

Referring to Table 3, compared to the single extracts of Comparative Examples 1 to 5, the mixed extracts of Examples 1 to 3 exhibited a higher inhibitory activity against nitric oxide (NO) production and had excellent antioxidant and anti-inflammatory activities. In addition, compared to the extract of Example 1, the extracts of Examples 2 and 3, which were prepared using ethanol extraction, had more excellent anti-inflammatory activities.

EXPERIMENTAL EXAMPLE 3

Evaluation of Antimicrobial Activity

The antimicrobial activities of the samples obtained according to the examples and the comparative examples were evaluated. *Propionibacterium acnes* KCTC 3314 was used as a published strain, and triclosan, a chemical synthetic antimicrobial agent, was used as a positive control.

*Propionibacterium acnes* KCTC 3314 was streaked onto a tryptic soy agar medium containing 5% sheep blood and incubated for about 2 to 3 days. Bacterial concentration was $1 \times 10^8$ cells/mL when the turbidity of the bacteria was equal to the turbidity of 0.5 McFarland Nephelometer Standard (1% barium chloride (0.05 ml)+1% sulfuric acid (9.95 ml)).

Each sample was diluted to 2ml of BHI broth at a concentration of 0 to 2,000 ppm using a 100-ppm dilution interval. Then, the diluted sample was inoculated with 20

µL, of the bacteria-containing solution at a cell density of 1×10⁸ cells/mL and cultured for 48 hours. The minimum concentration that inhibits bacterial growth based on turbidity was defined as the minimum inhibitory concentration (MIC), and the results are shown in Table 4 below.

TABLE 4

| Classification | Minimum inhibitory concentration (MIC) (ppm) |
|---|---|
| Example 1 | 600 |
| Example 2 | 520 |
| Example 3 | 450 |
| Comparative Example 1 | 1,200 |
| Comparative Example 2 | 1,400 |
| Comparative Example 3 | 1,550 |
| Comparative Example 4 | 1,650 |
| Comparative Example 5 | 1,450 |
| Triclosan | 400 |

Referring to Table 4, compared to triclosan, a positive control, the mixed extracts of Examples 1 to 3 exhibited a slightly weaker antimicrobial effect, but exhibited a remarkably superior antimicrobial effect as compared to the extracts of Comparative Examples 1 to 5.

In particular, the extracts of Examples 2 and 3, which were obtained by using ethanol extraction, had better antimicrobial effects against dandruff-inducing microorganism, compared to the extract of Example 1.

EXPERIMENTAL EXAMPLE 4

Evaluation of Effect of Relieving Atopic ermatitis

Compositions for external skin application containing each of the samples obtained according to the examples and the comparative examples were evaluated for the effect of relieving atopic dermatitis. Each of the samples was formulated into cream having the same composition, and the samples of Examples 1 to 3 and the samples of Comparative Examples 1 to 5 were different.

Eighty women aged 30 to 50 years were applied with each of the creams of the examples and the comparative examples, and the degree of relief of atopic dermatitis was evaluated.

Eighty women who had similar dermatitis symptoms were divided into 8 groups each consisting of 10 individuals. The cream was applied to the whole face for 12 weeks twice a day at a temperature of 24 to 26° C. and a humidity of 75%.

At the end of the test, for subjective assessment of efficacy, participants were asked to fill out a questionnaire. In the questionnaire, symptoms of atopic dermatitis were classified as "pruritus", "dryness", "keratinization", "dandruff", "erythema", "turgidity", "skin crack", "oozing and eczema", and "lichenification". Based on the questionnaire survey, the degree to which each symptom was relieved was evaluated. The results obtained were averaged to evaluate the relieving effect of atopic dermatitis symptoms individually. The evaluation results are shown in Table 5 below.

TABLE 5

| Sample | Remarkable relief (person) | Slight relief (person) | No relief (person) | Worsened (person) |
|---|---|---|---|---|
| Example 1 | 6 | 3 | 1 | — |
| Example 2 | 7 | 2 | 1 | — |
| Example 3 | 8 | 1 | 1 | — |
| Comparative Example 1 | 3 | 4 | 2 | 1 |
| Comparative Example 2 | 2 | 4 | 3 | 1 |
| Comparative Example 3 | 3 | 3 | 3 | 1 |
| Comparative Example 4 | 3 | 3 | 2 | 2 |
| Comparative Example 5 | 2 | 4 | 2 | 2 |

Referring to Table 5, compared to the single extracts of Comparative Examples 1 to 5, the mixed extracts of Examples 1 to 3 exhibited more excellent atopic dermatitis relieving effects.

In addition, compared to the extract of Example 1, the extracts of Examples 2 and 3, which were prepared using ethanol extraction, significantly relieved the symptoms of atopic dermatitis, and had excellent skin soothing effects.

The aforementioned description of the present invention is provided by way of example and those skilled in the art will understood that the present invention can be easily changed or modified into other specified forms without change or modification of the technical spirit or essential characteristics of the present invention. Therefore, it should be understood that the aforementioned examples are only provided by way of example and not provided to limit the present invention. For example, each of constituents described as a single form may be separately implemented and, similarly, constituents described as being separated may be implemented in a combined form.

It should be understood that the scope of the present invention is defined by the following claims and the invention is to cover all modifications, equivalents, and alternatives falling within the spirit and scope of the invention as defined by the claims.

It should be understood that the effects of the present invention are not limited to the effects described above, and include all effects that can be deduced from the description of the invention or the composition of the invention described in the claims.

When the composition for external skin application according to one aspect of the invention is used, through interaction of the active ingredients contained in the mixed extract, the skin health of the user can be improved, and the skin soothing effect can be maximized.

What is claimed is:

1. A composition for external skin application for relieving atopic dermatitis, comprising a mixed extract consisting of a *Bifidobacterium*-fermented extract, a *Citurs unshiu* peel extract, a *Laminaria japonica* extract, a *Camellia Japonica L.* extract, and an *Artemisia argyi* extract as an active ingredient.

2. The composition according to claim 1, wherein the mixed extract contains 10 to 20 parts by weight of the *Bifidobacterium*-fermented extract, 10 to 20 parts by weight of the *Citurs unshiu* peel extract, 10 to 20 parts by weight of the *Laminaria japonica* extract, 10 to 20 parts by weight of the *Camellia Japonica L.* extract, and 10 to 20 parts by weight of the *Artemisia argyi* extract.

3. The composition according to claim 1, wherein the mixed extract is contained in an amount of 0.5 to 10.0% by weight.

4. The composition according to claim 1, wherein
the mixed extract is extracted using one or more solvents selected from the group consisting of purified water, a lower alcohol having 1 to 4 carbon atoms, acetone, ethyl acetate, butyl acetate, and 1,3-butylene glycol.

5. The composition according to claim 4, wherein the lower alcohol is 60 to 90% (v/v) ethanol.

6. The composition according to claim 1, wherein the composition has antioxidant, anti-inflammatory, and antimicrobial activities.

7. The composition according to claim 1, wherein the composition is formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

8. The composition according to claim 2, wherein the composition has antioxidant, anti-inflammatory, and antimicrobial activities.

9. The composition according to claim 3, wherein the composition has antioxidant, anti-inflammatory, and antimicrobial activities.

10. The composition according to claim 4, wherein the composition has antioxidant, anti-inflammatory, and antimicrobial activities.

11. The composition according to claim 5, wherein the composition has antioxidant, anti-inflammatory, and antimicrobial activities.

12. The composition according to claim 2, wherein the composition is formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

13. The composition according to claim 3, wherein the composition is formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

14. The composition according to claim 4, wherein the composition is formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

15. The composition according to claim 5, wherein the composition is formulated into one or more selected from the group consisting of softening lotion, astringent lotion, nutritional lotion, lotion, nutritional cream, massage cream, essence, eye cream, cleansing cream, cleansing foam, cleansing water, pack, spray, and powder.

* * * * *